US00PP36029P2

(12) United States Plant Patent
Werner et al.

(10) Patent No.: US PP36,029 P2
(45) Date of Patent: Jul. 23, 2024

(54) ***CERCIS* PLANT NAMED 'NC2017-113'**

(50) Latin Name: *Cercis canadensis*
Varietal Denomination: NC2017-113

(71) Applicant: North Carolina State University, Raleigh, NC (US)

(72) Inventors: Dennis James Werner, Raleigh, NC (US); Leanne M. Kenealy Atkins, Durham, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 18/399,398

(22) Filed: Dec. 28, 2023

(51) Int. Cl.
*A01H 5/02* (2018.01)
*A01H 6/54* (2018.01)

(52) U.S. Cl.
USPC ..... Plt./216

(58) Field of Classification Search
USPC ..... Plt./216
CPC ... A01H 5/02; A01H 5/12; A01H 5/00; A01H 6/54
See application file for complete search history.

(56) References Cited

U.S. PATENT DOCUMENTS

PP17,161 P3 10/2006 Woody

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct variety of *Cercis* plant, referred to by its cultivar name, 'NC2017-113', is disclosed. The new variety is characterized by its white-colored flowers. The new variety is also characterized by its small, thick, glossy, and green-colored foliage. A moderately slow growing and compact growth habit is displayed.

3 Drawing Sheets

Latin name of genus and species of plant claimed: *Cercis canadensis.*

Variety denomination: 'NC2017-113'.

BACKGROUND OF THE INVENTION

The present invention relates to a new and distinct cultivar of *Cercis* plant botanically known as *Cercis canadensis* and hereinafter referred to by the cultivar name 'NC2017-113'.

The new cultivar originated in a controlled breeding program in Raleigh, North Carolina in March 2010.

The new *Cercis* cultivar is the result of a controlled cross wherein two parents were crossed which previously had been studied in the hope that they would contribute the desired characteristics. The female parent (i.e., the seed parent) of the new cultivar was *Cercis* 'Texas White' (not patented) and is characterized its white flowers, upright and rounded growth habit, and green foliage color. The male parent (i.e., the pollen parent) of the new cultivar is *Cercis* 'Ace of Hearts', U.S. Plant Pat. No. 17,161, and is characterized by its violet-colored flowers and compact habit.

The parentage of the new variety can be summarized as follows:

'Texas White' x 'Ace of Hearts'

The seeds resulting from the above pollination were sown and small plants were obtained which were physically and biologically different from each other. Selective study in summer of 2017 in a controlled environment in Jackson Springs, North Carolina resulted in the identification of a single plant of the new variety, which was selected for its white-colored flowers, small, thick, and glossy, green-colored foliage, and compact growth habit.

The new variety has been found to undergo asexual propagation in Belvidere, Tennessee by chip budding. This asexual reproduction has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'NC2017-113' as a new and distinct cultivar of *Cercis* plant:

(a) White-colored flowers,
(b) Small, thick, glossy, and green-colored foliage; and
(c) Compact growth habit.

The new variety of the present invention can readily be distinguished from its ancestors. More specifically, plants of the new cultivar differ from plants of 'Texas White' (i.e., the seed parent) in having a profusion of flowers and reduced internode length. In addition, plants of 'Ace of hearts' (i.e., the pollen parent) display violet-colored flowers, whereas plants of the new variety display white-colored flowers.

Moreover, the new variety can be readily distinguished from other similar non-parental varieties. Of the many commercially available *Cercis* cultivars, the most similar in comparison to the new cultivar is 'Royal White'(not patented). However, plants of the new cultivar differ from plants of 'Royal White' in at least the following characteristic:

1. Plants of the new cultivar have a more compact growth habit than plants of 'Royal White'.

2. Plants of the new cultivar have thicker and glossier leaves than plants of 'Royal White'.

BRIEF DESCRIPTION OF THE PHOTOGRAPHS

The accompanying photographs show, as nearly true as it is reasonably possible to make the same in color illustrations of this type, typical growth habit, flowering and foliage characteristics of the new cultivar. Colors in the photographs differ slightly from the color values cited in the detailed description, which accurately describes the colors of 'NC2017-113'. The plants in the photographs were taken at the Sandhills Research Station in Jackson Springs, North Carolina.

DETAILED BOTANICAL DESCRIPTION

Figure 1:
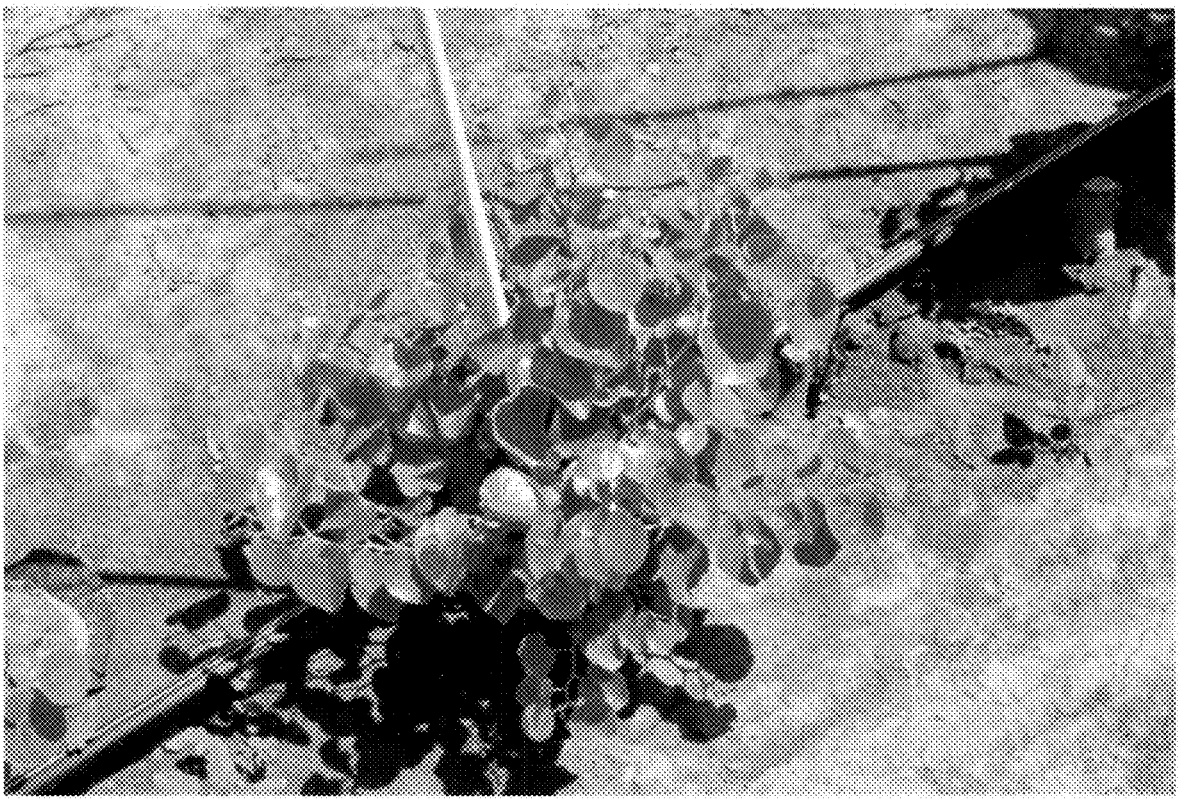
FIG. 1 illustrates a side view of 'NC2017-113, photograph taken Aug. 6, 2019.
Figure 2:
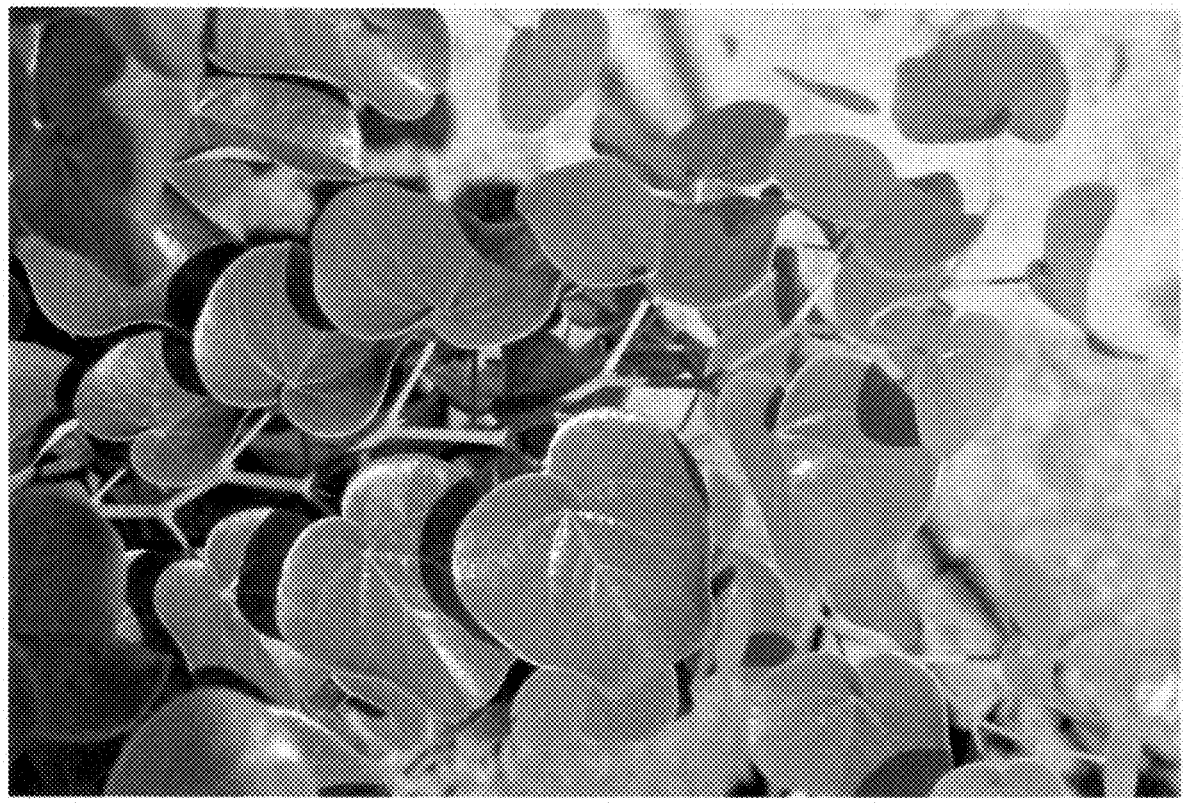
FIG. 2 illustrates a close up of the foliage of 'NC2017-113', photograph taken Aug. 6, 2019.
Figure 3:
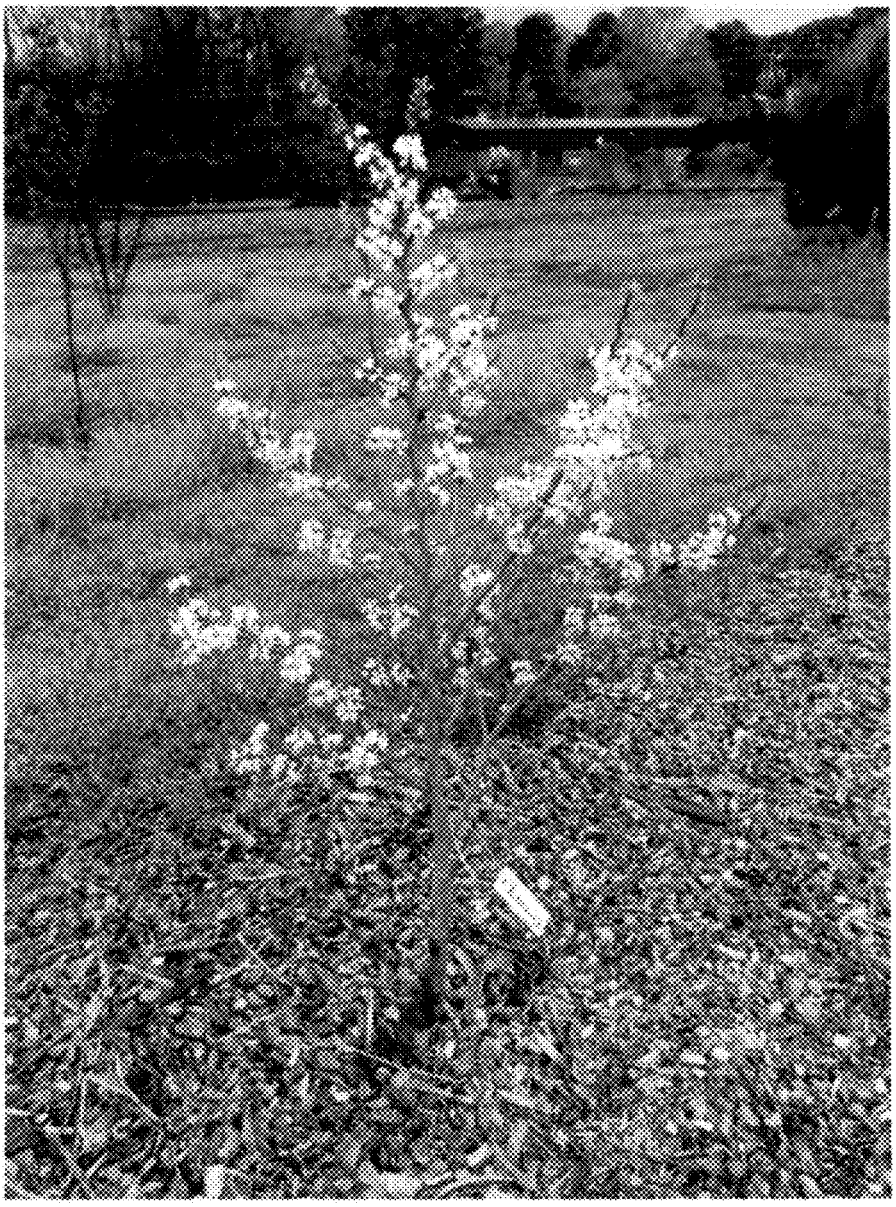
FIG. 3 illustrates a side view of a 'NC2017-113' when flowering, photograph taken Mar. 31, 2021.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used.

The following descriptions and measurements describe plants produced from chip budding and grown outside in Cochranville, Pennsylvania. Plants were approximately three years of age. Measurements and numerical values represent averages of typical plants.

Botanical classification: *Cercis canadensis* cultivar NC2017-113.

Parentage:

*Female parent.*—*Cercis* 'Texas White' (not patented).

*Male parent.*—*Cercis* 'Ace of Hearts', U.S. Plant Pat. No. 17,161.

Propagation:

*Type.*—Chip budding.

Plant description:

*Type.*—Deciduous perennial tree.

*Growth habit and general appearance.*—Moderately slow growing, compact tree.

*Commercial crop time.*—Approximately 1.5 years from budding to finish as a 2 to 3-foot tree.

*Hardiness.*—USDA Zone 6b.

*Size.*—Height of 3-year-old tree: Approximately 5 feet. Width: Approximately 5.7 feet.

*Trunk.*—Texture: slightly rough. Color: N200A.

*Branches.*—Densely branched. Branching habit: multi-branching, weeping architecture. Strength: Moderately strong. Diameter of one-year old growth: Approximately 5.0 mm. Stem Length of one-year old shoots: 22.5 cm. Internode length: 2.0 cm on average. Stem Shape: Circular. Growth pattern: slightly zigzag, deviating less than 5 degrees from vertical at each node. Texture of new growth: Slightly rugose. Color of young stem: N199A. Color of mature stem: previous seasons growth is N200A. Lenticel: numerous, tiny. Lenticel length: Less than 1.0 mm. Lenticel shape: circular to slightly elongate. Lenticel color: 197B.

Foliage description:

*General description.*—Type: Deciduous. Arrangement: Alternate.

*Leaves.*—Shape of mature leaves: Cordate. Apex: Distinctly pointed. Base: Cordate. Margin: Entire. Length to base of sinus: Approximately 4.5 cm. Length to end of lobe: Approximately 5.5 cm. Sinus indentation: Approximately 0.8 cm. Width: Approximately 5.2 cm. Texture of upper and lower surfaces: Slightly rugose. Venation pattern: Reticulate. Color of upper surface of mature foliage: 137A with indistinguishable venation. Color of under surface of mature foliage: 137B with venation of 147C. Color of upper and lower surfaces of immature foliage: 146B with indistinguishable venation. Fragrance: None detected.

*Petiole.*—Length: Approximately 2.8 cm. Diameter: Approximately 1.0 mm. Texture: Smooth, glabrous. Color: 137A.

Flowering description:

*Flowering season.*—Flowers in early spring for about 2-3 weeks depending on weather conditions.

*General description.*—Form: Fasicle. Flower Arrangement: Sessile clusters. Symmetry: Bilateral symmetry. Type: Papilionaceous. Quantity per cluster: 10 per cluster on average. Flower length: 7.0 mm on average. Flower width across wings at anthesis: 4.0 mm on average. Flower depth (bottom of keel petals to top of wings): 5.0 mm on average. Fragrance: None noticeable.

*Bud just before opening.*—Shape: slightly elongate. Diameter: Approximately 2.0 mm. Length: Approximately 4.0 mm. Color: 155B. Texture: Glabrous.

*Petals.*—Quantity: 5, unfused. Texture of upper and lower surfaces: Glabrous. Color of banner, wings, and keel base when first and fully open: 155C. Color of keel tip when first and fully open: 155C. Banner length: 6.0 mm. Banner diameter (at midsection): 2.0 mm. Wing length: 5.0 mm. Wing diameter (at midsection): 2.0 mm. Keel length: 6.0 mm. Keel diameter (at midsection): 3.0 mm. Apex shape for banner, wing, and keel: Rounded. Base shape for banner, wing, and keel: narrow. Margin for banner, wing, and keel: Entire.

*Calyx.*—Shape: Vase-shaped. Diameter: Approximately 2.0 mm at top of hypanthium. Length: Approximately 2.0 mm. Color of outer surface: 193A. Texture of inner and outer surfaces: Glabrous.

*Sepals.*—Arrangement: Fused. Length: Approximately 2.0 mm. Diameter 3.0 mm at tip, 1.0 mm at base. Length: 2.0 mm. Color: 192D.

*Pedicel.*—Strength: Strong. Shape: Round. Length: Approximately 5.0 mm. Diameter: Less than 1.0 mm. Texture: Glabrous. Color: 144D.

*Reproductive organs.*—Androecium: Stamen quantity per flower: 10 on average, unfused. Stamen length: Approximately 5.0 mm. Stamen width: Less than 1.0 mm. Anther shape: Round. Anther color: 160D. Filament length: Approximately 4.0 mm. Filament width: Less than 1.0 mm. Filament color: 155C. Pollen amount: Sparse. Pollen color: 11B. Gynoecium: Pistil length: Approximately 6.0 mm on average. Pistil width: Less than 1.0 mm. Pistil texture: Glabrous. Stigma shape: Round. Stigma color: 145C. Stigma length: Less than 1.0 mm. Stigma width: Less than 1.0 mm. Style shape: Round. Style width: Less than 1.0 mm. Style color: 144A. Ovary position: Superior. Ovary shape: Elongate. Ovary length: Less than 1.0 mm. Ovary width: Less than 1.0 mm. Ovary color: 143A.

*Seed production.*—None observed to date.

*Disease and pest resistance.*—Plants of the new *Cercis* have not been noted to be resistant to pathogens and pests common to *Cercis*.

We claim:

1. A new and distinct cultivar of *Cercis* plant named 'NC2017-113', substantially as herein illustrated and described.

* * * * *